US009820957B2

(12) United States Patent
Orndorff et al.

(10) Patent No.: US 9,820,957 B2
(45) Date of Patent: Nov. 21, 2017

(54) METHODS OF TREATING AUTOIMMUNITY (71) Applicants: IM Therapeutics, Inc., Broomfield, CO (US); The Regents of the University of Colorado, a body corporate, Denver, CO (US)

(72) Inventors: Steve Orndorff, Broomfield, CO (US); Aaron Michels, Centennial, CO (US); Peter Gottlieb, Englewood, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 15/466,026

(22) Filed: Mar. 22, 2017

(65) Prior Publication Data
US 2017/0273927 A1  Sep. 28, 2017

Related U.S. Application Data (60) Provisional application No. 62/312,702, filed on Mar. 24, 2016.

(51) Int. Cl.
| A61K 31/198 | (2006.01) |
| A61K 9/00 | (2006.01) |
| A61K 45/06 | (2006.01) |
| G01N 33/564 | (2006.01) |
| A61K 38/28 | (2006.01) |

(52) U.S. Cl.
CPC .......... *A61K 31/198* (2013.01); *A61K 9/0053* (2013.01); *A61K 38/28* (2013.01); *A61K 45/06* (2013.01); *G01N 33/564* (2013.01); *G01N 2800/042* (2013.01)

(58) Field of Classification Search
CPC .................................................. A61K 31/198
See application file for complete search history.

(56) References Cited

U.S. PATENT DOCUMENTS

| 4,207,890 A | 6/1980 | Mamajek et al. |
| 4,434,153 A | 2/1984 | Urquhart et al. |
| 4,691,018 A | 9/1987 | Mori et al. |
| 4,735,804 A | 4/1988 | Caldwell et al. |
| 4,758,436 A | 7/1988 | Caldwell et al. |
| 4,767,627 A | 8/1988 | Caldwell et al. |
| 5,415,994 A | 5/1995 | Imrich et al. |
| 5,424,193 A | 6/1995 | Pronovost et al. |
| 5,475,033 A | 12/1995 | Ohmori et al. |
| 5,594,100 A | 1/1997 | Wegman |
| 5,780,055 A | 7/1998 | Conte et al. |
| 6,001,567 A | 12/1999 | Brow et al. |
| 6,207,197 B1 | 3/2001 | Illum et al. |
| 7,144,569 B1 | 12/2006 | Anderson et al. |
| 7,749,503 B2 | 7/2010 | Tobia et al. |
| 8,314,210 B2 | 11/2012 | Wucherpfennig et al. |
| 9,629,848 B2 | 4/2017 | Eisenbarth et al. |
| 2002/0150914 A1 | 10/2002 | Andersen et al. |
| 2004/0096734 A1 | 5/2004 | Calundann et al. |
| 2004/0137514 A1 | 7/2004 | Steenbakkers |
| 2004/0253276 A1 | 12/2004 | Sato et al. |
| 2004/0265327 A1 | 12/2004 | Grassetti et al. |
| 2005/0222270 A1 | 10/2005 | Olney et al. |
| 2007/0021341 A1 | 1/2007 | Sela et al. |
| 2007/0196369 A1 | 8/2007 | Hoogenboom et al. |
| 2008/0194462 A1 | 8/2008 | Wucherpfennig et al. |
| 2008/0214656 A1 | 9/2008 | Lim et al. |
| 2011/0245334 A1 | 10/2011 | Du et al. |
| 2012/0171212 A1 | 7/2012 | Eisenbarth et al. |
| 2012/0195929 A1 | 8/2012 | Eisenbarth et al. |
| 2013/0017262 A1 | 1/2013 | Mullen et al. |
| 2014/0050807 A1 | 2/2014 | Leighton |

FOREIGN PATENT DOCUMENTS

| WO | WO 94/01775 | 1/1994 |
| WO | WO 94/29696 | 12/1994 |
| WO | WO 99/67641 | 12/1999 |
| WO | WO 00/38650 | 7/2000 |
| WO | WO 00/39587 | 7/2000 |
| WO | WO 01/64183 | 9/2001 |
| WO | WO 03/070752 | 8/2003 |
| WO | WO 2004/007528 | 1/2004 |
| WO | WO 2005/085323 | 9/2005 |
| WO | WO 2010/141883 | 12/2010 |
| WO | WO 2012/162697 | 11/2012 |
| WO | WO 2016/191634 | 12/2016 |

OTHER PUBLICATIONS

Aldomet® (Methyldopa) Product Label (NDA 13-400/S-086, 2004, pp. 3-8).*
Grigoriadis et al. Case Reports in Obstetrics and Gynecology, vol. 2013, Article ID 150278, 2 pages.*
Rosenblum et al. Sci. Transl. Med. Author manuscript; available in PLC Jun. 18, 2014, pp. 1-20.*
Au et al. Biochem. J., 1972, vol. 129, pp. 1-10.*
Stern et al. Arzneinittel-Forschung, 1970, vol. 20, No. 5, pp. 727-728 (Abstract Attached).*
Auclair et al. Fundamental & Clinical Pharmacology, 1988, vol. 2, No. 4, pp. 283-293 (Abstract Attached).*
Ames et al., "Stereochemical Course In Vivo of Alpha-Methyldopa Decasrboxylation in Rat Brains," Biochem. Pharmacology, 1977, vol. 26(19), pp. 1757-1762.
International Search Report and Written Opinion for International (PCT) Application No. PCT/US2017/23571, dated Jul. 3, 2017, 17 pages.

(Continued)

Primary Examiner — James D. Anderson
(74) Attorney, Agent, or Firm — Sheridan Ross P.C.

(57) ABSTRACT

Methods of treating, ameliorating, or inhibiting the development of autoimmune diseases by modulating the binding of MHC class II molecules to antigenic peptides or fragments of antigenic peptides of the autoimmune disease. The binding may be modulated by the administration of D-α-methyldopa, or pharmaceutical compositions comprising therapeutically effective amounts of D-α-methyldopa.

16 Claims, 7 Drawing Sheets

(56) References Cited

OTHER PUBLICATIONS

U.S. Appl. No. 14/341,767, filed Jul. 26, 2014, Eisenbarth et al.
U.S. Appl. No. 15/355,738, filed Nov. 18, 2016, Eisenbarth et al.
U.S. Appl. No. 15/495,132, filed Apr. 24, 2017, Eisenbarth et al.
Aharoni et al., "Immunomodulation of experimental allergic encephalomyelitis by antibodies to the antigen-la complex," Nature, 1991, vol. 351, pp. 147-150.
Aoki et al., "NOD mice and autoimmunity," Autoimmun. Rev., 2005, vol. 4, pp. 373-379.
Boulard et al., "An interval tightly linked to but distinct from the h2 complex controls both overt diabetes (iddl6) and chronic experimental autoimmune thyroiditis (ceatl) in nonobese diabetic mice," Diabetes, 2002, vol. 51, pp. 2141-2147.
Bresson et al., "Moving towards efficient therapies in type 1 diabetes: To combine or not to combine?," Autoimmun Rev, 2007, vol. 6(5), pp. 315-322, 11 pages.
Chung et al., "Competitive Inhibition In Vivo and Skewing of the T Cell Repertoire of Antigen-Specific CTL Priming by an Anti-Peptide-MHC Monoclonal Antibody," J. Immunol., 2001, vol. 167, pp. 699-707.
Corper et al., "A structural framework for deciphering the link between I-Ag7 and autoimmune diabetes," Science, 2000, vol. 288, pp. 505-511.
Crawford et al., "Mimotopes for Alloreactive and Conventional T Cells in a Peptide-MHC Display Library," PLoS. Biol., 2004, vol. 2, p. 0523-0533.
Faideau et al., "Expression of preproinsulin-2 gene shapes the immune response to preproinsulin in normal mice," J. Immunol., 2004, vol. 172, pp. 25-33.
Fairbrother et al., "Effects of Three Plant Growth Regulators on the Immune Response of Young and Aged Deer Mice Peromyscus Maniculatus," Arch. Environ. Contam, Toxicol., 1986, vol. 15, pp. 265-275.
Fife et al., "Insulin-induced remission in new-onset NOD mice is maintained by the PD-1-PD-L1 pathway," J. Experimental Med., 2006, vol. 203, pp. 2737-2747.
Fujisawa et al., "MHC-linked susceptibility to type 1 diabetes in the NOD mouse: further localization of Idd16 by subcongenic analysis," Ann. NY Acad. Sci., 2006, vol. 1079, pp. 118-121.
Fukushima et al., "Combined insulin B:9-23 self-peptide and polyinosinic-polycytidylic acid accelerate insulitis but inhibit development of diabetes by increasing the proportion of CD4+Foxp3+ regulatory T cells in the islets in non-obese diabetic mice," Biochemical and Biophysical Research Communications, 2008, vol. 367, pp, 719-724.
Hattori et al., "The NOD mouse: recessive diabetogenic gene within the major histocompatibility complex," Science, 1986, vol. 231, pp. 733-735.
Homann et al., "An immunologic homunculus for type 1 diabetes," J. Clin, Invest., 2006, vol. 116, pp. 1212-1215.
Hovhannisyan et al., "The role of HLA-DQ8 beta57 polymorphism in the anti-gluten T-cell response in coeliac disease," Nature, 2008, vol. 456, pp. 534-538.
Hurtenback, "Prevention of Autoimmune Diabetes in Non-Obese Diabetic Mice by Treatment with a Class II Major Histocompatibility Complex-blocking Peptide," Journal of Experimental Medicine, 1993, vol. 177(5), pp. 1499-1504.
Kachapati et al.,"The Non-Obese Diabetic (NOD) Mouse as a Model of Human Type 1 Diabetes." Animal Models in Diabetes Research. Methods in Molecular Biology, 2012, vol. 933, pp. 3-16, 29 pages.
Kanagawa et al., "The role of I-Ag7 β chain in peptide binding and antigen recognition by T cells," Int Immunol., 1998, vol. 9, pp. 1523-1526.
Kobayashi et al., "Conserved T cell receptor alpha-chain induces insulin autoantibodies," Proc. Natl. Acad. Sci. USA, 2008, vol. 105, pp. 10090-10094.
Lee et al., "Structure of a human insulin peptide-HLA-DQ8 complex and susceptibility to type 1 diabetes." Nature Immunology, 2001, vol. 2(6), pp. 501-507.

Levisetti et al., "The Insulin-Specific T Cells of Nonobese Diabetic Mice Recognize a Weak MHC-Binding Segment in More Than One Form." Journal of Immunology, 2007, vol. 178(10), pp. 6051-6057.
Levisetti et al., "Weak proinsulin peptide-major histocompatibility complexes are targeted in autoimmnne diabetes in mice," Diabetes, 2008, vol. 57, pp. 1852-1860.
Li et al., A computer screening approach to immunoglobulin superfamily structures and interactions: Discovery of small non-peptidic CD4 inhibitors as novel immunotherapeutics, Proc. Natl. Acad. Sci. USA, 1997, vol. 94, pp. 73-78.
Mareeva et al., "Antibody Specific for the Peptide-Major Histocompatibility Complex," J. Biol. Chem., 2004, vol. 279(43), pp. 44243-44249.
Masteller et al., "Peptide-MHC Class II Dimers as Therapeutics to Modulate Antige-Specific T Cell Responses in Autoimmune Diabetes," J. Immunol., 2003, vol. 171, pp. 5587-5595.
Merfeld et al., "The effect of pH and concentration on alpha-methyldopa absorption in man," J Pharrn Pharmacol., 1986, vol. 38, pp. 815-822.
Mordes et al., "Rat Models of Type 1 Diabetes: Genetics, Environment, and Autoimmunity," ILAR Journal, 2004, vol. 45, No. 3, pp. 278-291.
Moriyama et al., "Evidence for a primary islet autoantigen (preproinsulin 1) for insulitis and diabetes in the nonobese diabetic mouse," Proc, Natl Acad. Sci, USA, 2003, vol. 100, pp. 10376-10381.
Nakayama et al., "Prime role for an insulin epitope in the development of type 1 diabetes in NOD mice," Nature, 2005, vol. 435(7039), pp. 220-223, author manuscript, 10 pages.
Nakayama et al., "Priming and effector dependence on insulin B:9-23 peptide in NOD islet autoimmnnity," J. Clin. Invest., 2007, vol. 117, pp. 1835-1843.
National Cancer Institute, Developmental Therapeutics Program website, retrieved from https://dtp.cancer.gov/, retrieved on May 15, 2017, 1 page.
NSC 10408-Commpound Summary (CID 407900), PuhChem, 2005, retrieved from http://pubchem.ncbi.nlm.nih.gov/summary/summary.cgi?cid=407906, retrieved on Aug. 24, 2012, 5 pages.
Oikonmakos et al., "Allosteric inhibition of glycogen phosphorylase alpha by the Ppotential Aantidiabetic drug 3-isopropyl 4-(2-chorophenyl)-1,4-dihydro-1-ethyl-2-methyl-pyridine-3,5,6-tricarboxylate," Protein Science, 1999, vol. 8, pp. 1930-1945.
Pietropaolo et al., "Primer: Immunity and Autoimmunity," Diabetes, 2008, vol. 57, pp. 2872-2882.
Puri et al., "Modulation of the Immune Response in Multiple Sclerosis," J. Immunol., 1997, vol. 158, pp. 2471-2476.
Renwick et al., "The Absorption and Conjugation of Methyldopa in Patients with Celiac and Crohn's Diseases During Treatment," Br. J. Clin. Pharmac., 1983, vol. 16, pp. 77-83.
Salvati et al., "Recombinant human interleukin 10 suppresses gliadin dependent T cell activation in ex vivo cultured coeliac intestinal mucosa," Gut, 2005, retrieved from gut.bmj.com, retrieved on Aug. 21, 2012, vol. 54, pp. 46-53.
Scheen, "Pathophysiology of type 2 diabetes," Acta Clinica Belgica, 2003, vol. 58(6), pp. 335-341.
Sjoerdsma et al., "Studies on the Metabolism and Mechanism of Action of Methyldopa," Circulation, 1963, vol. 28, pp. 492-502.
Sosinowski et al., "Type 1 diabetes: primary antigen/peptide/register/trimolcular complex," Immunol. Res., 2013, vol. 55, pp. 270-276.
Suri et al., "The Murine Diabetogenic Class II Histocompatibility Molecule I-A (g7): Structural and Functional Properties and Specificity of Peptide Selection," Adv. Immunal., 2005, vol. 88, pp. 235-265.
Thomson et al , "FK 506: a novel immunosuppressant for treatment of autoimmune disease: Rationale and preliminary clinical experience," Springer Semin Immunopathol. 1993, vol. 14(4), 31 pages.
Todd et al., "A molecular basis for MHC class II associated autoimmunity," Science, 1988, vol. 240, pp. 1003-1009.
Wallis et al., "Type 1 Diabetes in the BB rat: A polygenic disease," Diabetes, 2009, vol. 58(4), pp. 1007-1017.

(56) References Cited

OTHER PUBLICATIONS

WebMD 2014 Diabetes Mellitus: Types, Symptoms, Causes, Treatments: accessed online Oct. 27, 2015; http://www.webmd.com/diabetes/guide/types-of-diabetes-mellitus, p. 1-7.
Wicker et al., "Type 1 diabetes genes and pathways shared by humans and NOD mice," J. Autoimmun., 2005, vol. 25 (Suppl), pp. 29-33.
Wucherpfennig, "Insights into autoimmunity gained from structural analysis of MHC-peptide complexes," Current Opinion in Immunology, 2001, vol. 13, pp. 650-656.
Zhang et al., "Immunization with an insulin peptide-MHC complex to prevent type 1 diabetes of NOD mice," Diabetes Meta Res Rev, 2011, vol. 27, pp. 784-789.
Zhong et al., "Production, specificity, and functionality of monoclonal antibodies to specific peptide-major histocompatibility complex class II complexes formed by processing of exogenous protein," Proc. Natl. Acad. Sci. USA, 1997, vol. 94, pp. 13856-13861.
International Search Report and Written Opinion for International (PCT) Application No. PCT/US2017/23571, dated Sep. 21, 2012, 9 pages.
International Search Report and Written Opinion for International (PCT) Application No. PCT/US2012/039849, dated Sep. 21, 2012, 9 pages.
International Preliminary Report on Patentability for International (PCT) Application No. PCT/US2012/039849, dated Dec. 5, 2013, 7 pages.
International Search Report and Written Opinion for International (PCT) Application No. PCT/US2016/034527, dated Aug. 25, 2016, 13 pages.
Official Action for U.S. Appl. No. 14/119,926, dated May 21, 2015 6 pages, Restriction Requirement.
Official Action for U.S. Appl. No. 14/119,926, dated Nov. 3, 2015 19 pages.
Notice of Allowance for U.S. Appl. No. 14/119,926, dated Jul. 26, 2016 7 pages.
Notice of Allowance for U.S. Appl. No. 14/119,926, dated Aug. 19, 2016 5 pages.

\* cited by examiner

METHODS OF TREATING AUTOIMMUNITY

RELATED APPLICATION DATA

This application claims the benefit of priority to U.S. Provisional Patent Application Ser. No. 62/312,702, filed Mar. 24, 2016, which is incorporated herein by reference.

TECHNICAL FIELD

This disclosure relates to the use of methyldopa in the prevention or treatment of autoimmune diseases, such as autoimmune diabetes.

BACKGROUND

Autoimmune disorders are diseases caused by the body producing an inappropriate immune response against its' own tissues, in which the immune system creates T lymphocytes and autoantibodies that attack one's own cells, tissues, and/or organs. Researchers have identified 80-100 different autoimmune diseases and suspect at least 40 additional diseases have an autoimmune basis.

Autoimmune disorders are classified into two types, organ-specific (directed mainly at one organ) and non-organ-specific (widely spread throughout the body). Examples of organ-specific autoimmune disorders are insulin-dependent Type 1 diabetes, which affects the pancreas, Celiac disease, which affects the lining of the small intestine, Hashimoto's thyroiditis and Graves' disease, which affect the thyroid gland, pernicious anemia, which affects the stomach, Addison's disease, which affects the adrenal glands, chronic active hepatitis, which affects the liver, and myasthenia gravis, which affects the muscles. Examples of non-organ-specific autoimmune disorders are rheumatoid arthritis, multiple sclerosis, and lupus.

One of the most prevalent organ-specific autoimmune diseases, Type 1 diabetes, is characterized by the production of autoantibodies that target the insulin-secreting pancreatic beta cells. The disease pathogenesis involves T cell infiltration into the islets of the pancreas, which subsequently destroys insulin producing beta cells, and results in overt symptoms of disease. In most cases, T cells can respond to an antigen only when the antigen is properly presented by an antigen-presenting cell expressing the appropriate major histocompatibility complex (MHC) molecule. Thus, T cell immune response to an antigen requires recognition by the T cell receptor of an antigen coupled to a MHC molecule, and this recognition requires the assembly of a tri-molecular complex between an antigen, a MHC molecule, and a T cell receptor.

Evidence strongly indicates that insulin/proinsulin is a key or primary auto-antigen in the development of type 1 diabetes in the NOD (non-obese diabetic) mouse model. Initial cloning of T cells from islets of NOD mice led to the discovery that the native insulin B chain amino acids 9-23 (B: 9-23 insulin peptide) is the dominant antigenic peptide epitope presented by the class II MHC molecule I-A. Mice lacking the native B: 9-23 sequence fail to develop diabetes and development of insulin autoantibodies and insulitis are markedly decreased. Restoring the native B: 9-23 sequence with an islet transplant (but not bone marrow transplant) or peptide immunization, or a native proinsulin transgene, restores anti-insulin autoimmunity and generates CD4 T cells that cause diabetes.

The major genetic determinant of islet autoimmunity and diabetes in human and animal models are genes within the major histocompatibility complex, and in particular, class II MHC alleles. The NOD mouse's unique sequence of IA (homologous to human DQ) and lack of expression of I-E (shared with many standard mouse strains) are essential for the development of diabetes.

Celiac disease is an autoimmune disorder of the small intestine that affects between 1 in 100 and 1 in 300 people depending on the region of the world. The disease occurs in people of all ages and causes pain and discomfort in the digestive tract, chronic constipation and diarrhea, failure to thrive in children, anemia, and fatigue. The disease is caused by a reaction to gliadin, a prolamin (gluten protein) found in wheat, and other common grains such as barley and rye, in which the immune system cross-reacts with the small-bowel tissue, causing an inflammatory autoimmune reaction. The only known effective treatment is a lifelong gluten-free diet.

There exists a need in the art for safer and more effective methods for treating or slowing the progression or development of autoimmune disorders, such as autoimmune diabetes (type 1 diabetes, T1D) and Celiac disease (gluten sensitivity). This disclosure addresses these needs by providing molecules and formulations useful in the treatment and prevention of autoimmune diseases while achieving other advantages discussed more fully below.

SUMMARY

The present disclosure provides new uses of D-α-methyldopa to prevent or reduce the binding of T cell receptors to peptides presented by class II MHC molecules, as well as therapeutic uses of D-α-methyldopa and pharmaceutical compositions comprising D-α-methyldopa to prevent or slow the formation of autoimmune diabetes (type 1 diabetes; T1D) and Celiac disease in an individual.

Many autoimmune disorders have strong associations with specific HLA alleles, including T1D, which is the immune-mediated form of diabetes resulting from the chronic autoimmune destruction of pancreatic beta cells. Approximately 90% of all individuals with T1D have DQ8 and/or DQ2 alleles, with a predominance of DQ8 (DQA*0301, DQB*0302) in 50-60% of all T1D patients. DQ8 and DQ2 alleles confer significant disease risk while another DQ allele, DQ6 (DQB*0602), provides dominant protection from diabetes development. DQ8 and DQ2 are also the predominant HLA alleles in Celiac disease, present in about 99% of all Celiac disease patients. Thus, individuals with DQ8 and/or DQ2 alleles who have not yet manifested clinical disease may be at risk of developing T1D and/or Celiac disease, and/or may be suspected of suffering from T1D or Celiac disease.

T1D is now a predictable disease with the measurement of islet autoantibodies (insulin, glutamic acid decarboxylase, insulinoma associated antigen 2, and zinc transporter 8), but it cannot yet be prevented. Furthermore, T1D incidence is increasing 3-5% every year in industrialized countries with children less than five years of age being the most affected. Additionally, there is currently no known cure for T1D, and treatment for this disease consists of lifelong administration of insulin. Despite treatment with insulin therapy, long-term complications, including nephropathy, retinopathy, neuropathy, and cardiovascular disease can result. While the progress to complete insulin dependence occurs quickly after clinical onset, initially after diagnosis the pancreas is still able to produce a significant amount of insulin. The Diabetes Control and Complications Trial (DCCT) found that 20% of patients studied who were within 5 years of diagnosis, had remaining insulin production (0.2-0.5 pmol/ml). Thus, immunologic intervention during the window following diagnosis could save beta cell function, delay the onset of T1D, and reduce reliance on insulin administration.

Class II major histocompatability molecules are the primary susceptibility locus for many autoimmune diseases, including type 1 diabetes. "Diabetogenic" alleles HLA-DQ8 in humans and I-A$^{g7}$ in non-obese diabetic (NOD) mice confer disease risk, and both molecules share structural similarities. The present inventors have evaluated a novel pathway to identify safe and specific therapies to treat the underlying T cell autoimmunity in T1D. This pathway involves blocking allele-specific MHC class II antigen presentation as a treatment to inhibit DQ8-mediated T cell responses. DQ8 confers significant disease risk by presenting epitopes of insulin and other beta cell antigens to effector CD4 T cells. The present inventors have surprisingly found that D-α-methyldopa blocks or reduces insulin and gliadin peptide presentation to T cells. Without intending to be bound by theory, it is believed that D-α-methyldopa occupies a pocket along the DQ8 (DQA*03:01, DQB*03:02) peptide binding groove, thereby blocking DQ8 restricted T cell responses in vitro, and inhibiting DQ8 antigen presentation in vivo. Blocking HLA-DQ8 antigen presentation in this way may help preserve beta cell mass (and endogenous insulin production) in new onset T1D and may also prevent or delay T1D onset in multiple islet autoantibody-positive individuals (i.e., 2 or more islet autoantibodies), 70-90% of whom develop diabetes within 10 years.

Thus, the present disclosure provides methods of reducing the binding of T cell receptors to insulin/proinsulin peptides presented by class II MHC molecules, to treat or slow the progression or development of T1D or Celiac disease in an individual suffering from, or at risk of developing, T1D or Celiac disease, comprising administering D-α-methyldopa to such individuals. The present disclosure also provides pharmaceutical compositions containing D-α-methyldopa that are particularly useful in such methods of treating or slowing the progression or development of T1D.

One aspect of this disclosure is a method of inhibiting an autoimmune disease by administering to an individual in need of such treatment, a therapeutically effective amount of D-α-methyldopa that inhibits the T cell response to the targeted antigenic peptide of the autoimmune disease. The D-α-methyldopa inhibits the binding of a DQ8 peptide to an MEW class II molecule for presentation to CD4+ T cells, thereby slowing the development or progression of T1D or Celiac disease. The inhibition of the binding of a DQ8 peptide to an MHC class II molecule may result from a distortion of the spatial orientation of the complex so that the DQ8 antigen is not properly presented to T cells.

A related aspect provides a method of selectively treating T1D in an individual, including selecting an individual for treatment with D-α-methyldopa on the basis of the individual having at least two islet autoantibodies detectable in a blood sample from the individual, and selectively administering D-α-methyldopa to that individual.

In any of the methods of this disclosure, the individual may have been tested for the presence of autoantibodies to insulin or proteins within beta cells, wherein the presence of such antibodies in the individual is indicative of the presence or likely development of T1D. Thus, a related aspect of this disclosure provides methods of treating an individual found to have such autoantibodies by administering D-α-methyldopa to the individual.

Another aspect of this disclosure provides methods of monitoring and adjusting the dosage of D-α-methyldopa administered to an individual suffering from, or at risk of developing, an autoimmune disorder (such as T1D or Celiac disease) including receiving a blood sample from an individual suffering from, or at risk of developing, the autoimmune disorder who has been administered α-methyldopa and determining the DQ8-stimulated response of IL-2 T cells in the blood sample. The DQ8-stimulated response of IL-2 T cells in the blood sample is compared to a control level of DQ8-stimulated response of IL-2 T cells in blood samples from at least one of a patient suffering from the autoimmune disease and a control or 'wild type' individual known to be free of the autoimmune disease. The dosage and/or the frequency of the D-α-methyldopa administered to the individual is increased if the DQ8-stimulated response of IL-2 T cells in the blood sample from the individual is statistically similar to the DQ8-stimulated response of IL-2 T cells from the baseline level in the T1D patient.

Other aspects of the invention will be set forth in the accompanying description of embodiments, which follows and will be apparent from the description. However, it should be understood that the following description of embodiments is given by way of illustration only, as various changes and modifications within the spirit and scope of the invention will become apparent to those skilled in the art and are encompassed within the scope of this disclosure.

BRIEF DESCRIPTION OF DRAWINGS

FIG. 1A shows the DQ8-.

DESCRIPTION OF EMBODIMENTS

The present disclosure is drawn to methods of treating or slowing the progression or development of an autoimmune disease by reducing the binding, or altering the presentation of, antigenic peptides, or fragments of antigenic peptides, presented by an MHC class II molecule (DQ8) by the administration of D-α-methyldopa to an individual suffering from, or at risk of developing, an autoimmune disease.

The term "insulin peptide" is used to denote a peptide fragment of an insulin protein. Although the fragment is typically a subset of the amino acid sequence of the insulin protein, an insulin peptide may contain the entire amino acid sequence of a naturally-occurring insulin protein.

The terms "individual" or "subject" are used interchangeably herein. The terms "individual" and "individuals" refer to an animal, such as a mammal, including a non-primate (e.g., a cow, pig, horse, cat, dog, rat, and mouse) and a primate (e.g., a monkey such as a cynomolgus monkey, a chimpanzee and a human), and a human. In certain embodiments, the subject is refractory or non-responsive to current treatments for an autoimmune disease.

"Tissue" means any biological sample taken from any individual, preferably a human. Tissues include blood, saliva, urine, biopsy samples, skin or buccal scrapings, and hair.

Persons of skill in the art will appreciate that blood plasma drug concentrations obtained in individual subjects will vary due to inter-patient variability in the many parameters affecting drug absorption, distribution, metabolism and excretion. For this reason, unless otherwise indicated, when a drug plasma concentration is listed, the value listed is the calculated mean value based on values obtained from a group of subjects tested.

The term "bioavailability" refers to the extent to which, and sometimes the rate at which, the active moiety (drug or metabolite) enters systemic circulation, thereby gaining access to the site of action.

"AUC" is the area under the plasma concentration-time curve and is considered to be the most reliable measure of bioavailability. It is directly proportional to the total amount of unchanged drug that reaches the systemic circulation.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

The term "therapeutically-effective amount" of D-α-methyldopa means an amount effective to modulate the formation or progression of autoimmune diseases (including T1D and Celiac disease) in an individual.

Most amino acids are chiral (designated as 'L' or 'D' wherein the 'L' enantiomer is the naturally occurring configuration) and can exist as separate enantiomers. The USP standard methyldopa for antihypertensive therapy is the 'L' enantiomer of α-methyldopa: L-α-Methyl-3,4-dihydroxyphenylalanine (hereinafter "L-α-methyldopa" available commercially under the tradenames ALDOMET™, ALDORIL™, DOPAMET™, DOPEGYT™), and has the chemical structure:

L-α-methyldopa is an alpha-adrenergic agonist (selective for α2-adrenergic receptors) that was developed as a psychoactive drug and has been used extensively as a sympatholytic or antihypertensive.

The 'D' enantiomer of α-methyldopa (D-α-Methyl-3,4-dihydroxyphenylalanine; hereinafter "D-α-methyldopa" is also referred to in the literature as "3-Hydroxy-α-methyl-D-tyrosine"; "D-3-(3,4-Dihydroxyphenyl)-2-methylalanine"; "(+)-α-Methyldopa"; "D-(3,4-Dihydroxyphenyl)-2-methylalanine"; "D-Methyldopa"), has the chemical structure:

Prior to the present disclosure, D-α-methyldopa was considered to have no pharmacologic activity (see, for example, U.S. Patent Publication No. 2011/0245334, filed Dec. 10, 2009, to Du et al.). Gillespie, et al. (1962, *Clinical and Chemical Studies with α-Methyl-Dopa in Patients with Hypertension*, Circulation 25:281-291) were the first to describe the lack of pharmacological activity in the 'D' isomer and suggest using only the 'L' enantiomeric form for hypertension. Similarly, Sjoerdsma, et al., (1963, *Studies on the Metabolism and Mechanism of Action of Methyldopa*, Circulation, 28:492-502) showed that patients treated with the D enantiomer did not decarboxylate the D enantiomer to α-methyl-dopamine, whereas α-methyl-dopamine did appear in the urine of the same patients treated with the L enantiomer, indicating metabolism of this L enantiomer. Au et al. (1972, *The Metabolism of $^{14}$C-Labelled α-Methyldopa in Normal and Hypertensive Human Subjects*, Biochem. J., 129:1-10) more extensively described the marked differences in metabolism of the two enantiomers in humans, and found that the D isomer was "much less readily absorbed than the active L isomer." These authors also cite other supporting literature references, including a suggestion that there is an optically specific, active transport mechanism that may be responsible for this difference in adsorption. Additionally, Renwick et al. (1983, *The Absorption and Conjugation of Methyldopa in Patients with Coeliac and Crohn's Diseases During Treatment*, Br. J. Clin. Pharmac., 16:77-83) showed that absorption rates of methyldopa are different between normal individuals and those with certain GI diseases such as Celiac and Crohn's disease.

D-α-methyldopa may be purchased commercially (see, for example, Toronto Research Chemicals, catalogue M303790). D-α-methyldopa may also be prepared in ways well known to one skilled in the art of organic synthesis, including, for example, by resolution of the racemic form by recrystallization techniques, by synthesis from optically-active starting materials, by chiral synthesis, or by chromatographic separation using a chiral stationary phase. The resolution of methyldopa, may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981. Additionally, several methods of effectively and efficiently testing the enantiomeric purity of α-methyldopa are known, as described in Martens, J., et al., *Resolution of Optical Isomers by Thin-Layer Chromatography: Enantiomeric Purity of Methyldopa*, Arch. Pharm. (Weinheim) 319:572-74 (1986); and Gelber, L. R., Neumeyer, J. L., *Determination of the Enantiomeric Purity of Levodopa, Methyldopa, Carbidopa and Tryptophan by the Use of Chiral Mobile Phase High-Performance Liquid Chromatography*, J. Chromatography, 257:317-26 (1983).

The invention is based on the inventors' surprising discovery that, contrary to the accepted understanding that L-α-methyldopa comprises all of the pharmacologic activity of α-methyldopa, D-α-methyldopa actually possesses nearly equivalent activity in reducing the presentation of antigenic peptides, or fragments of antigenic peptides, by MHC class II molecules in autoimmune diseases, such as T1D or Celiac disease. This unexpected discovery is particularly fortuitous as L-α-methyldopa, which is a competitive inhibitor of the enzyme DOPA decarboxylase (also known as aromatic L-amino acid decarboxylase), is associated with many adverse side effects, including depression and even suicidal ideation, as well as nightmares, anhedonia, dysphoria, anxiety, decreased desire, drive, and motivation, lethargy, malaise, sedation or drowsiness, cognitive and memory impairment, sexual dysfunction including impaired libido, dizziness, lightheadedness, or vertigo, xerostomia, headache, migraine, myalgia, arthralgia, paresthesia, parkinsonian symptoms such as muscle tremors, rigidity, hypokinesia, and/or balance or postural instability, hypotension, hepatotoxicity, pancreatitis, haemolytic anaemia, and myelotoxicity. These effects are believed, at least in part, to be due to metabolites of L-α-methyldopa. As D-α-methyldopa presumably is not metabolized, D-α-methyldopa is less likely to cause such adverse effects. This distinction also improves the window of therapeutic dosing of D-α-methyldopa compared to L-α-methyldopa.

D-α-methyldopa preparations, for use in the methods and compositions of this disclosure, are substantially free of the L-enantiomer of α-methyldopa. In the methods and compositions of this disclosure, the D-α-methyldopa compounds are at least 85%, 90%, 95%, 98%, 99% to 100% by weight of the D-enantiomer, the remainder comprising other chemical species or enantiomers. Thus, these D-α-methyldopa compositions contain less than 10%, less than 1%, or preferably less than 0.1%, by weight, of the L-enantiomer of α-methyldopa.

D-α-methyldopa can be formulated into pharmaceutical compositions using methods available in the art and provided in the appropriate pharmaceutical composition and administered by a suitable route of administration. The methods provided herein encompass administering pharmaceutical compositions containing D-α-methyldopa, if appropriate in the salt form, either used alone or in the form of a combination with one or more compatible and pharmaceutically acceptable carriers, such as diluents or adjuvants, or with another therapeutic agent. The second therapeutic agent can be formulated or packaged with the D-α-methyldopa. Of course, the second agent will only be formulated with the D-α-methyldopa, according to the judgment of those of skill in the art, as such co-formulation should not interfere with the activity of either agent or the method of administration.

The D-α-methyldopa and the second agent may be formulated separately. They may also be packaged together, or packaged separately, for the convenience of the medical practitioner. These additional agent(s) may include an anti-diabetic compound selected from at least one of an alpha-glucosidase inhibitor, a biguanide, a Dpp-4 inhibitor, a meglitinide, a sulfonylurea, a thiazolidinedione, or combinations of these agents.

In clinical practice the D-α-methyldopa may be administered by any conventional route, in particular orally or parenterally. In preferred embodiments, the D-α-methyldopa is administered orally, as solid or liquid compositions for oral administration, for example, as tablets, pills, hard gelatin capsules, powders or granules.

A composition provided herein is a pharmaceutical composition or a single unit dosage form. Pharmaceutical compositions and single unit dosage forms provided herein comprise a prophylactically or therapeutically effective amount of D-α-methyldopa and typically one or more pharmaceutically acceptable carriers or excipients. In this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Examples of suitable pharmaceutical carriers are described in "Remington's Pharmaceutical Sciences" by E. W. Martin.

A preferred formulation of this disclosure is a monophasic pharmaceutical composition suitable for oral administration for the treatment, prophylaxis, or slowing the progression of autoimmune diabetes, consisting essentially of a therapeutically-effective amount of D-α-methyldopa, and a pharmaceutically acceptable carrier.

Methods of Use

Provided herein are methods for the treatment and/or prophylaxis of an autoimmune disease in an individual. These methods include the treatment of an individual suffering from an autoimmune disease, such as T1D or Celiac disease, by the administration of an effective amount of D-α-methyldopa. These methods may encompass the step of administering to the individual in need of such treatment an amount of D-α-methyldopa effective for treating or delaying the development of an autoimmune disease, such as T1D or Celiac disease. The D-α-methyldopa may be in the form of a pharmaceutical composition or single unit dosage form, as described above.

This disclosure includes methods of treating or slowing the progression or development of autoimmune diabetes or Celiac disease by reducing the binding of WHC class II molecules to antigenic peptides or fragments of antigenic peptides of the autoimmune disease by the administration of D-α-methyldopa to individuals suffering from, or at risk of developing, autoimmune diabetes (T1D) or Celiac disease.

A specific method includes treating T1D in an individual comprising administering an effective amount of D-α-methyldopa to an individual in need of such treatment. Another method includes treating Celiac disease in an individual comprising administering an effective amount of D-α-methyldopa to an individual in need of such treatment.

Another method includes treating an individual at risk of developing T1D comprising administering an effective amount of D-α-methyldopa to the individual. Another method includes treating an individual at risk of developing Celiac disease comprising administering an effective amount of D-α-methyldopa to the individual. Thus, this disclosure provides for the use of D-α-methyldopa in the manufacture of a medicament for the treatment of T1D and the use of D-α-methyldopa in the manufacture of a medicament for the treatment of Celiac disease. This disclosure also provides D-α-methyldopa for use in the treatment of T1D, and D-α-methyldopa for use in the treatment of Celiac disease.

In these methods, the D-α-methyldopa may be administered orally to the individual. The D-α-methyldopa may be administered to an individual once daily, or more frequently. The D-α-methyldopa may be administered to an individual as a pharmaceutically acceptable salt, solvate or hydrate thereof. The D-α-methyldopa, or a pharmaceutically acceptable salt thereof, may be administered to an individual as a pharmaceutical composition described above.

In the methods of treating or slowing the progression or development of T1D of this disclosure, D-α-methyldopa or a pharmaceutically acceptable salt thereof, is administered to an individual suspected of suffering from, or at risk of developing T1D. Preferably, the administration to an individual diagnosed with T1D commences within 5 years of the initial diagnosis of T1D in the individual, or more preferably, within 1 year of the initial diagnosis of T1D in the individual, or more preferably, within 6 months of the initial diagnosis of T1D in the individual, or more preferably, within 1 month of the initial diagnosis of T1D in the individual.

In any of these methods, the individual may be administered a dosage of D-α-methyldopa, or a pharmaceutically acceptable salt, solvate or hydrate thereof, between about 50 mg and about 3000 mg of D-α-methyldopa per day. Preferably, the individual is administered a dosage of D-α-methyldopa between about 50 mg and about 1000 mg of D-α-methyldopa per day. The individual may be administered a dosage of D-α-methyldopa between about 250 mg and about 500 mg in an oral, immediate release dosage formulation at least twice daily. Typically, the D-α-methyldopa is administered in dosages ranging between 50 mg and 3000 mg per day. In most instances, the D-α-methyldopa may be initially administered at a dosage of 50 mg to 500 mg once, twice, or three times daily. These doses may be increased in patients with Crohn's or Celiac disease.

In any of these methods, in addition to D-α-methyldopa, the individual may also be administered an anti-diabetic compound, including at least one of an alpha-glucosidase inhibitor, a biguanide, a Dpp-4 inhibitor, a meglitinide, a sulfonylurea, a thiazolidinedione, or combinations of these agents.

In any of these methods, the individual may be between 1 year and 15 years of age. Alternatively, in these methods, the individual may be between 15 years and 30 years of age. Alternatively, in these methods, the individual may be older than 30 years of age.

Another aspect of these methods includes an initial determination of which patients may benefit from the administration of D-α-methyldopa (and, optionally, an anti-diabetic compound, as described above), prior to administration of D-α-methyldopa to individual determined to be in need of such treatment. As described above, DQ8 and DQ2 alleles confer significant risk of T1D and Celiac disease, while DQ6 allele provides dominant protection from diabetes development. Thus, individuals with DQ8 and/or DQ2 alleles are individuals at risk of developing T1D and/or Celiac disease. Additionally, individuals with islet autoantibodies (i.e., antibodies that specifically recognize insulin, glutamic acid decarboxylase, insulinoma associated antigen 2, or zinc transporter 8), or autoantibodies that recognize a MHC class II molecule bound to an insulin protein or to a gliadin peptide, or to insulin or gliadin peptide fragment(s), wherein the presence of such antibodies in the individual is indicative of the presence or likely development of T1D and/or Celiac disease in that individual. Such individual therefore may benefit from the methods of administering D-α-methyldopa, as described above.

The determination of which DQ8 or DQ2 alleles are present in an individual may enable a clinician to establish the subject's risk of developing an autoimmune disease.

For example, if the genotyping methods of this disclosure reveal a homozygous DQA*0301 or DQB*0302 genotype (two copies of one or both of these alleles) in the nucleic acid sample obtained from the individual, this finding indicates that the individual is more likely to develop T1D or Celiac disease. The clinician may then consider it beneficial to administer D-α-methyldopa in accordance with the methods of this disclosure. Additionally, an individual found to be heterozygous DQA*0301 or DQB*0302 genotype may still benefit from the administration of D-α-methyldopa. In this instance, the finding of a heterozygote genotype in the individual may be used to modify the dosage and/or dosing regimen of D-α-methyldopa to the individual, which may include reducing the dose or frequency of administration of D-α-methyldopa to the individual.

Alternatively, if the genotyping methods of this disclosure reveal homozygous wild type HLA alleles or protective alleles, such as DQB*0602, in the nucleic acid sample obtained from the individual, then the clinician may rule out an elevated risk of developing T1D or Celiac disease in the individual and consider different treatments or diagnoses for that individual.

A number of methods are available for analyzing and determining the DQ8 and/or DQ2 genotype in a subject, which can be applied to a nucleic acid sample obtained from a subject. Assays for detection of polymorphisms or mutations fall into several categories, including but not limited to, direct sequencing assays, fragment polymorphism assays, hybridization assays, and computer based data analysis. Protocols and kits or services for performing these general methods are commercially available and well known to those of skill in the art. In some embodiments, assays are performed in combination or in hybrid (e.g., different reagents or technologies from several assays are combined to yield one assay). Thus, the presence or absence of DQ8 and/or DQ2 alleles may be determined using direct sequencing. Alternatively or additionally, the DQ8 and/or DQ2 alleles may be determined using a PCR-based assay using oligonucleotide primers to amplify a DNA fragment containing the DQ8 and/or DQ2 polymorphism of interest. Alternatively or additionally, the DQ8 and/or DQ2 alleles may be determined using a fragment length polymorphism assay, such as a restriction fragment length polymorphism assay (RPLP), to detect a unique DNA banding pattern indicative of an DQ8 and/or DQ2 genotype based on cleaving the DNA at a series of positions is generated using an enzyme (e.g., a restriction endonuclease). Alternatively or additionally, the DQ8 and/or DQ2 alleles may be determined using a hybridization assay, wherein the genotype is determined based on the ability of the DNA from the sample to hybridize to a complementary DNA molecule (e.g., an oligonucleotide probe). The DQ8 and/or DQ2 polymorphisms of interest may be detected using a DNA chip hybridization assay, in which a series of oligonucleotide probes, designed to be unique to a given single nucleotide polymorphism, are affixed to a solid support, and the nucleic acid sample from the subject is contacted with the DNA "chip" and hybridization is detected. Alternatively or additionally, the DQ8 and/or DQ2 alleles may be determined using a "bead array" (such as those described in PCT Publications WO99/67641 and WO00/39587, each of which is herein incorporated by reference). Alternatively or additionally, the DQ8 and/or DQ2 alleles may be determined using an assay that detects hybridization by enzymatic cleavage of specific structures (such as those assays described in U.S. Pat. No. 6,001,567, and Olivier, M., The Invader assay for SNP Genotyping, 2005 Mutat Res. June 3; 573 (1-2): 103-110, both of which are incorporated herein by reference).

Genomic DNA samples are usually, but need not be, amplified before being analyzed. Genomic DNA can be obtained from any biological sample. Amplification of genomic DNA potentially containing an DQ8 and/or DQ2 polymorphism generates a single species of nucleic acid if the individual from whom the sample was obtained is homozygous at the polymorphic site, or two species of nucleic acid if the individual is heterozygous. RNA samples may also be subjected to amplification. In this case, amplification is typically, but not necessarily, proceeded by reverse transcription. Amplification of all expressed mRNA may also be performed (such as described in Innis M A et al., 1990, Academic Press, PCR Protocols: A Guide to Methods and Applications and Bustin SA 2000. Journal of Molecular Endocrinology, 25 Absolute quantification of mRNA using real-time reverse transcription polymerase chain reaction assays. pp. 169-193, which are hereby incorporated by reference in their entirety).

Any known method of analyzing a sample for an analyte can be used to practice the present invention, so long as the method detects the presence, absence, or amount of anti-islet antibodies. Examples of such methods include, but are not limited to, immunological detection assays and non-immunological methods (e.g., enzymatic detection assays). Additionally or alternatively, an binding compound is immobilized on a substrate, such as a microtiter dish well, a dipstick, an immunodot strip, or a lateral flow apparatus. A sample collected from a subject is applied to the substrate and incubated under conditions suitable (i.e., sufficient) to allow the formation of a complex between the binding compound and any anti-islet antibody present in the sample. Once formed, the complex is then detected. As used herein, the term "detecting complex formation" refers to identifying the presence of a binding compound complexed to an anti-islet antibody. If complexes are formed, the amount of complexes formed can, but need not be, quantified. Complex formation, or selective binding, between an anti-islet antibody and a binding compound can be measured (i.e., detected, determined) using a variety of methods standard in the art including, but not limited to, an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, a BIACORE™ assay (e.g., using colloidal gold), an immunodot assay (e.g., CMG's Immunodot System, Fribourg, Switzerland), and an immunoblot assay (e.g., a western blot), an phosphorescence assay, a flow-through assay, a chromatography assay, a PAGE-based assay, a surface plasmon resonance assay, a spectrophotometric assay, a particulate-based assay, and an electronic sensory assay. The assays may be used to give qualitative or quantitative results. The assay results can be based on detecting the entire antibody or fragments, or degradation products. Some assays, such as agglutination, particulate separation, and immunoprecipitation, can be observed visually (e.g., either by eye or by a machine, such as a densitometer or spectrophotometer) without the need for a detectable marker. A detectable marker can be conjugated to the compound or reagent at a site that does not interfere with the ability of the compound to bind anti-islet antibodies. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label, a metal sol label, a colored bead, a physical label, or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE™ NeutrAvidin). Means of detecting such markers are well known to those of skill in the art.

A tri-molecular complex between an insulin or gliadin antigen, a MHC molecule, and T cell receptor can be detected by contacting a biological sample from an individual with an antibody specific for the complex, wherein the antibody is conjugated to a detectable marker. A detectable marker can also be conjugated to a tri-molecular complex between an insulin or gliadin antigen, a MHC molecule, and T cell receptor such that contact of the labeled complex with a biological sample from an individual can detect the presence of antibodies to the complex present in the individual tested. Detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE™ NeutrAvidin).

A tri-molecular complex may be detected by contacting the complex with an indicator molecule. Suitable indicator molecules include molecules that can bind to the tri-molecular binding molecule complex. As such, an indicator molecule can comprise, for example, an antibody. Preferred indicator molecules that are antibodies include, for example, antibodies reactive with the antibodies from animals in which the anti-islet antibodies are produced. An indicator molecule itself can be attached to a detectable marker of the present invention. For example, an antibody can be conjugated to biotin, horseradish peroxidase, alkaline phosphatase or fluorescein. One or more layers and/or types of secondary molecules or other binding molecules capable of detecting the presence of an indicator molecule may be used. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

A lateral flow assay may be used for detection, examples of which are described in U.S. Pat. No. 5,424,193; U.S. Pat.

No. 5,415,994; WO 94/29696; and WO 94/01775 (all of which are incorporated by reference herein).

Once a biological sample from an individual has been analyzed to determine which allele of an DQ8 and/or DQ2 polymorphism is present, the individual can be selected, or identified, as likely or unlikely to develop, or at higher or lower risk of developing, T1D or Celiac disease. Such a selection is made using the results from the analysis step of the disclosed method.

Each publication or patent cited herein is incorporated herein by reference in its entirety. Additional objects, advantages, and novel features of this disclosure will become apparent to those skilled in the art upon examination of the following examples thereof, which are not intended to be limiting.

EXAMPLES

Example 1 Human T1D Treatment Study

Human leukocyte antigen (HLA) alleles confer significant genetic risk for type 1 diabetes (T1D) with recent studies implicating DQ8 in its pathogenesis, and DQ8 antigen presentation can be inhibited with methyldopa in animal models. In this pilot study, the inventors evaluated methyldopa treatment in 10 DQ8 positive human individuals with T1D, ages 18-46 years (mean 27) with less than 2 years of diabetes duration (mean 3 months). This was an open label phase 1b dose escalation study. All individuals tolerated low (500 mg BID) and moderate (500 mg TID) dosages of methyldopa, while 9/10 tolerated the high dose (2-3 g/day).

Figure 1A:
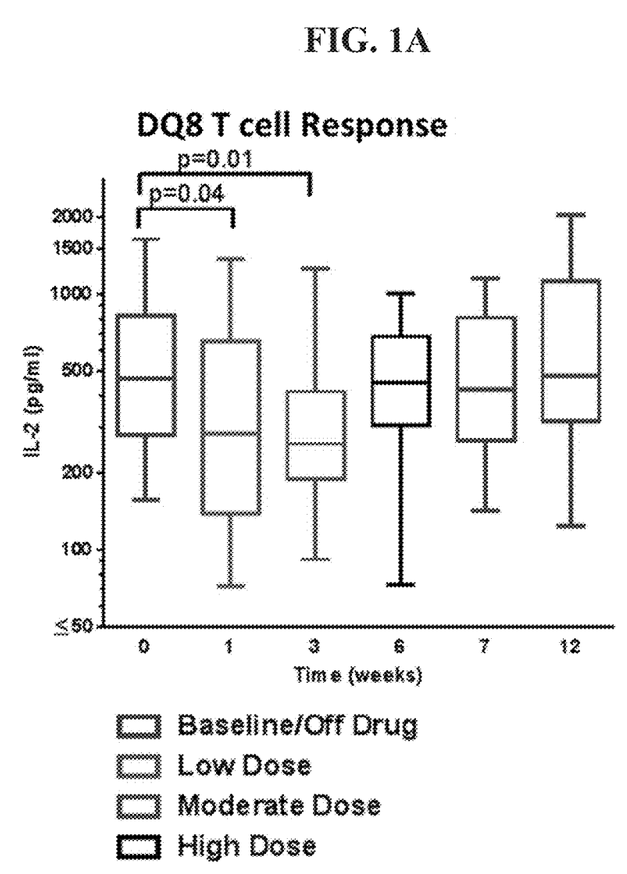
Figure 1B:
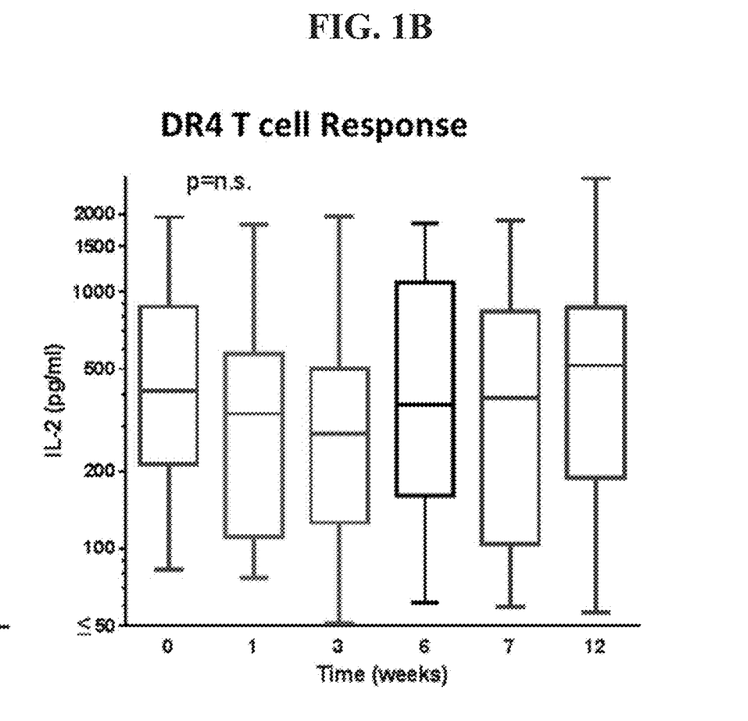
FIG. 1B shows the DR4-T cell responses, of T1D patients treated with varying doses of methyldopa, shown side-by-side for comparison.
Figure 2:
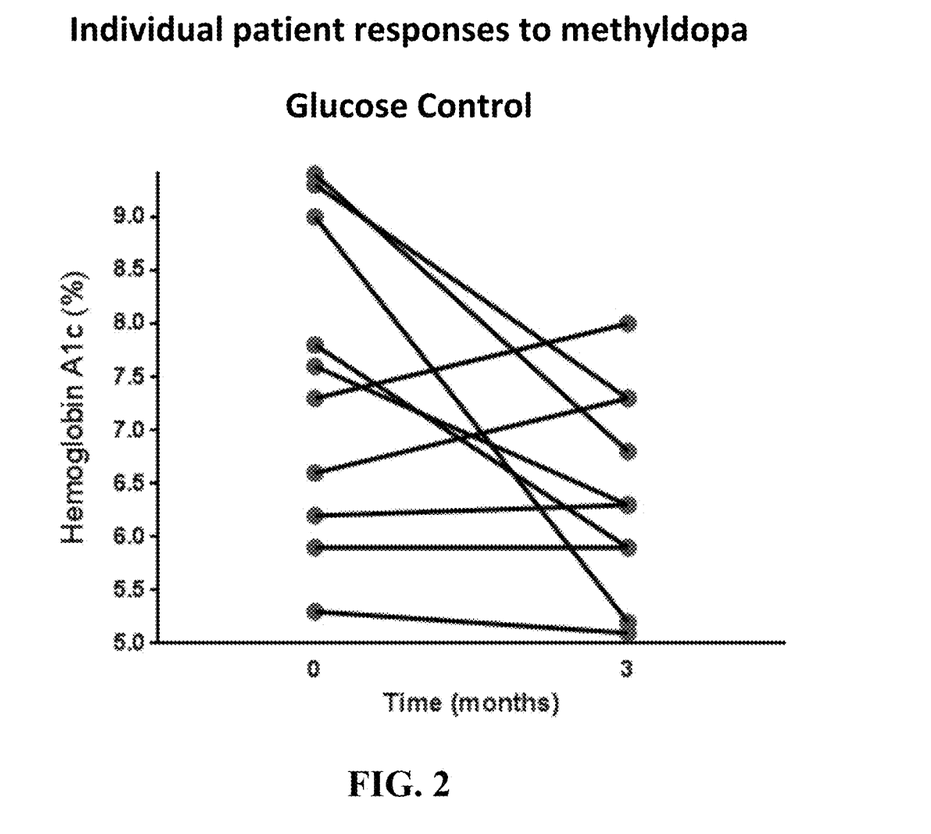
FIG. 2 shows the glucose control achieved in human T1D patients treated with methyldopa over 3 months.
Figure 3:
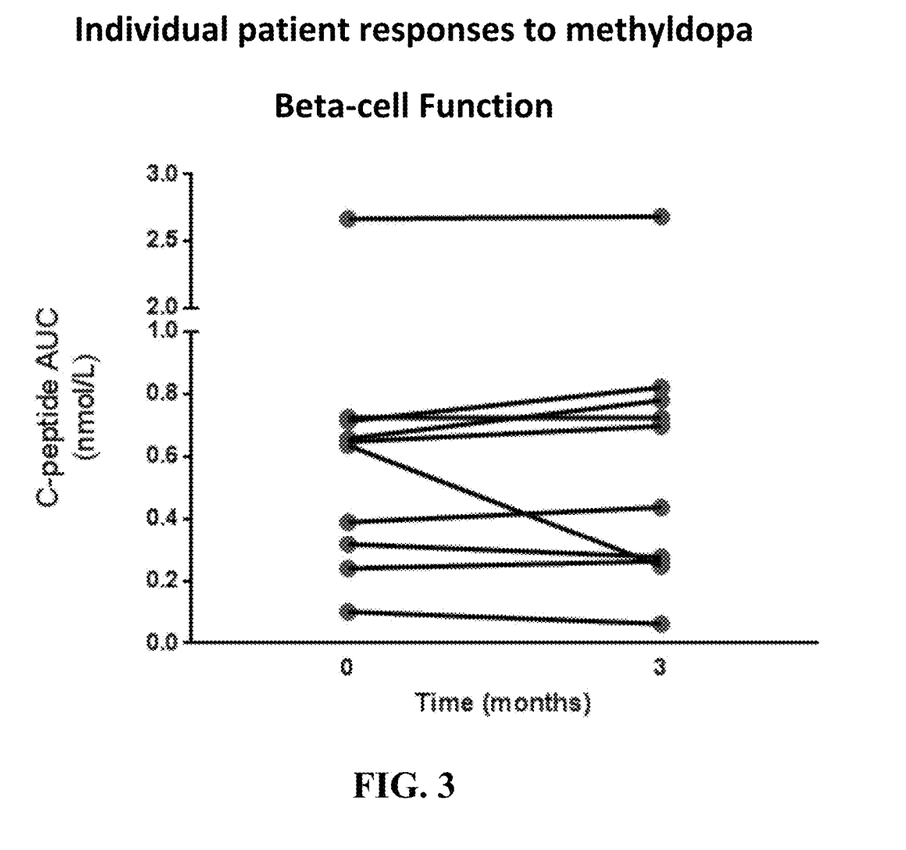
FIG. 3 shows the beta-cell function in human T1D patients treated with methyldopa over 3 months.

There was a dose-dependent reduction in DQ8-stimulated IL-2 T cell response at 1 (−32%) and 3 weeks (−39%), which returned to normal 6 weeks after stopping therapy (FIG. 1A). This response was specific for the DQ8-stimulated T cell response because DR4 T cell responses were minimally effected (FIG. 1B). The treated T1D patients had good glycemic control (FIG. 2). Additionally, the 2 hour AUC for C-peptide following a mixed meal tolerance test at 12 weeks was similar to baseline levels (FIG. 3). No serious adverse events (hypotension, DKA, or hypoglycemia) were reported throughout the study. This example demonstrates that methyldopa inhibits DQ8 antigen presentation in T1D.

Example 2 Enantiomers of α-methyldopa Similarly Inhibit DQ8 Restricted T Responses in vitro Inhibition of DQ8 antigen presentation by the D- and L-enantiomers of α-methyldopa was tested and compared in vitro. HLA-DQ8 antigen presenting cells were cultured with a fixed concentration of peptide and a concentration of D- or L-α-methyldopa for 4 hours. TCR transductants were then added to each culture condition and cultured overnight. Secreted IL-2 from the TCR transductant was measured by ELISA for each condition.

Figure 4A:
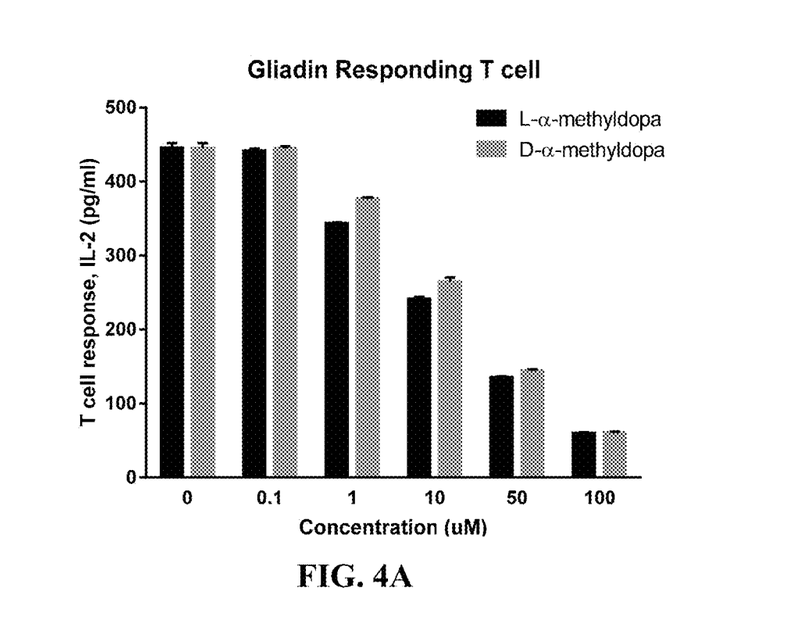
FIG. 4A shows dose-dependent inhibition of a gliadin-responsive CD4 T cell receptor (TCR) transductant by enantiomers of α-methyldopa.
Figure 4B:
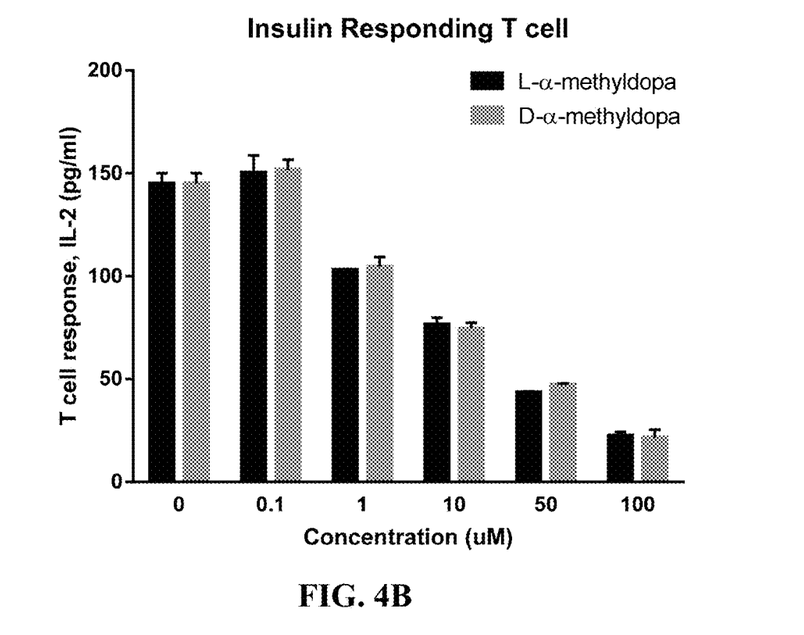
FIG. 4B shows a similar inhibition of an insulin responsive CD4 T cell receptor (TCR) transductant by the α-methyldopa enantiomers.

As shown in FIG. 4A, a gliadin-responsive CD4 T cell receptor (TCR) transductant was blocked in a dose-dependent manner with statistically similar $IC_{50}$ values between the α-methyldopa enantiomers. Similarly, as shown in FIG. 4B an insulin responsive CD4 T cell receptor (TCR) transductant was blocked in a dose-dependent manner with statistically similar $IC_{50}$ values between the α-methyldopa enantiomers. In these figures, 0 represents the TCR transductant response to peptide without the addition of α-methyldopa. No antigen IL-2 responses (negative control) were very low at <2 pg/ml. Results are presented as mean+/− SEM. These data demonstrate that the dose-dependent inhibitory effects of the D- and L-enantiomers of α-methyldopa on DQ8 antigen presentation in in vitro models of Celiac disease and T1D, are nearly identical.

Figure 5A:
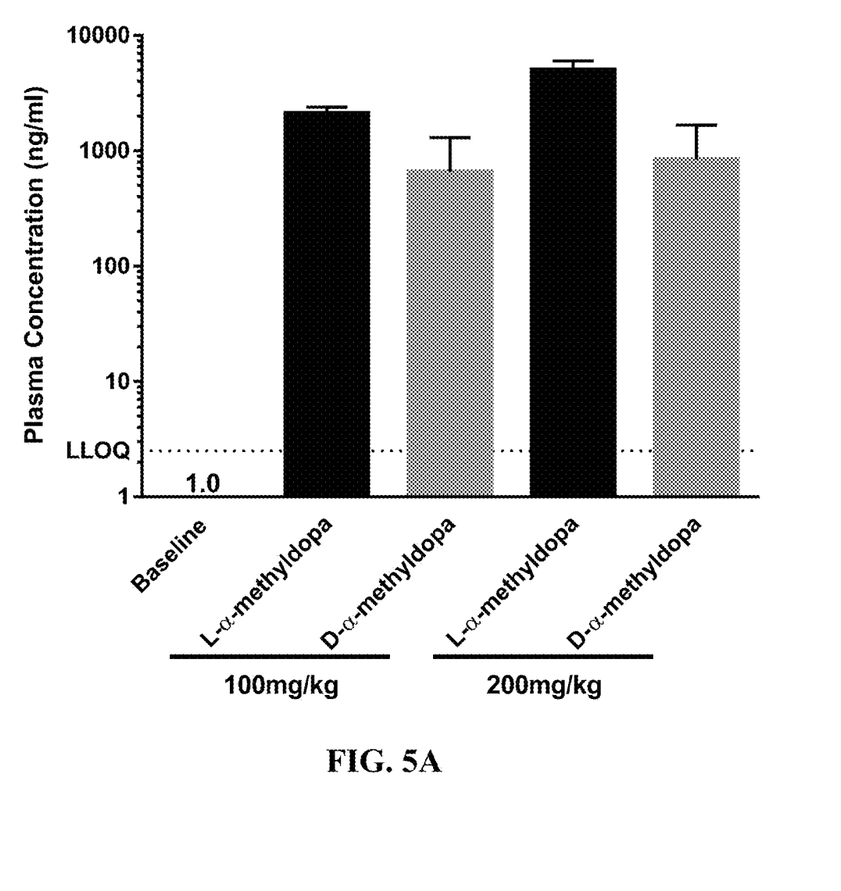
FIG. 5A shows an in vivo pharmacokinetic assessment of oral L- and D-α-methyldopa doses in HLA-DQ8 transgenic mice.
Figure 5B:
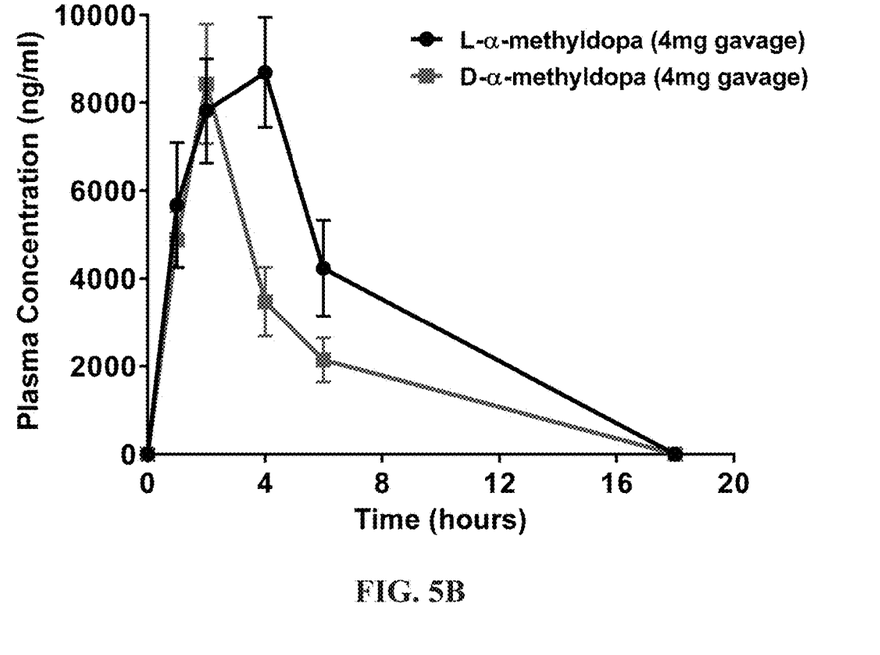
FIG. 5B shows a pharmacokinetic comparison of an oral L- and D-α-methyldopa dose in HLA-DQ8 transgenic mice.

Example 3 Pharmacokinetic and Pharmacodynamic Assessment of α-methyldopa Enantiomers in Mice Separate cohorts of HLA-DQ8 transgenic mice (n=2) were gavaged with a specific dose of L- and D-α-methyldopa, followed by the collection of plasma 90 minutes later. FIG. 5A shows the plasma concentrations of α-methyldopa as determined using HPLC-MS detection. Similarly, separate cohorts of mice (n=3) were gavaged with a specific enantiomer (D or L enantiomer) and dose (4 mg by gavage) of α-methyldopa followed by the collection of plasma at baseline, 1, 2, 4, 6, and 18 hours later. FIG. 5B shows the plasma concentrations of each enantiomer at these time points. In these PK studies the Lower Limit of Quantification (LLOQ) was <2.5 ng/ml. Results are presented as mean+/− SEM. These data demonstrate that the bioavailability of both the D- and L-enantiomer of α-methyldopa is nearly identical following oral administration in mammals, while the L-enantiomer has a slightly slower time to maximum plasma concentration (Tmax).

Figure 6:
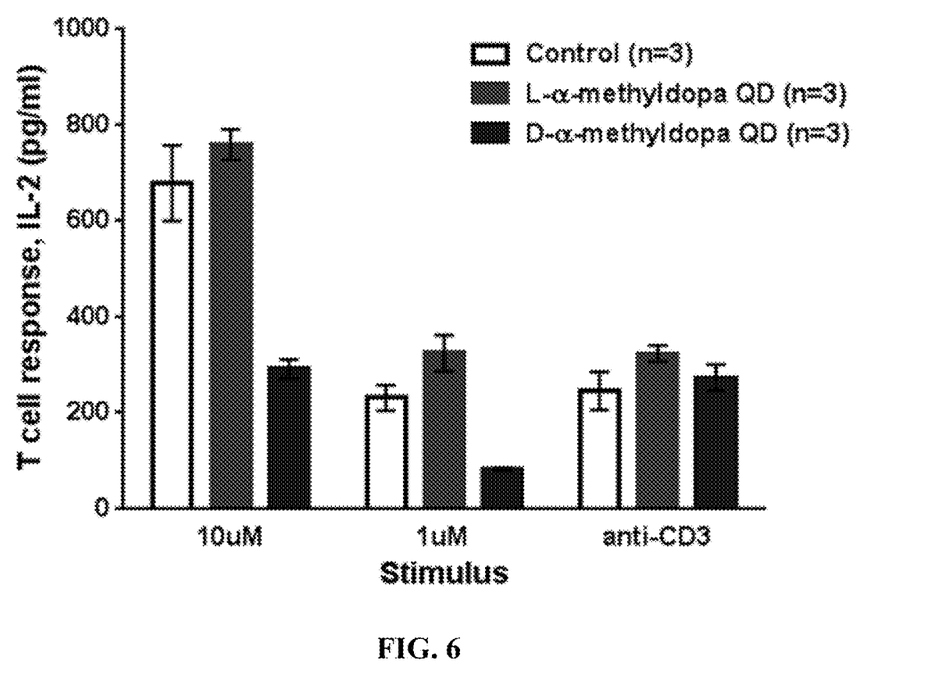
FIG. 6 shows an in vivo pharmacodynamic assessment of identical once-daily dosing of L- and D-α-methyldopa in HLA-DQ8 transgenic mice.

DQ8 transgenic mice (n=3 per group) were treated with 4 mg methyldopa by oral gavage daily for 5 days. Ex vivo splenocytes were used to stimulate a DQ8-restricted T cell to a deamidated gliadin peptide. As shown in FIG. 6, a positive control stimulus (anti-CD3) was not different between the groups, but inhibition of the T cell response is observed only for the D enantiomer. These data demonstrate that, despite similar bioavailability, the D-α-methyldopa enantiomer comprises T cell inhibitory activity in mammals at once daily dosing.

The foregoing description of the invention has been presented for purposes of illustration and description and is not intended to limit the invention to the form disclosed herein. Variations and modifications commensurate with the above teachings, and the skill or knowledge of the relevant art, are within the scope of this invention. It is intended that the appended claims be construed to include alternative embodiments to the extent permitted by the prior art.

What is claimed is:

1. A method of treating, ameliorating, or slowing the progression or development of an type 1 diabetes (T1D) selected from autoimmune diabetes or Celiac disease in an individual having a DQ8 allele by administering to an individual in need of such treatment, a therapeutically effective amount of D-α-methyldopa, or a pharmaceutically acceptable salt, solvate, or hydrate thereof.

2. The method of claim 1, wherein the autoimmune disease is type 1 diabetes (T1D).

3. The method of claim 1, wherein the D-α-methyldopa is administered as a pharmaceutical composition.

4. The method of claim 3, wherein the pharmaceutical composition is a single unit oral dosage form.

5. The method of claim 1, wherein the administration of D-α-methyldopa alters the presentation of insulin antigenic peptides to MHC class II molecules.

6. The method of claim 1, wherein the D-α-methyldopa is administered orally to the individual.

7. The method of claim 1, wherein the D-α-methyldopa is administered to an individual at least once daily.

8. The method of claim 2, wherein the D-α-methyldopa is administered to an individual after diagnosis of T1D in the individual.

9. The method of claim 1, wherein the individual is administered a dosage of D-α-methyldopa between about 50 mg and about 3000 mg of D-α-methyldopa per day.

10. The method of claim 1, wherein the individual is administered a dosage of D-α-methyldopa between about 50 mg and about 1000 mg of D-α-methyldopa per day.

11. The method of claim 1, wherein the individual is administered a dosage of D-α-methyldopa between about 50 mg and about 500 mg in an oral immediate release dosage formulation at least twice daily.

12. The method of claim 1, further comprising the administration of an anti-diabetic compound selected from at least one of insulin, an alpha-glucosidase inhibitor, a biguanide, a DPP-4 inhibitor, a meglitinide, a sulfonylurea, a thiazolidinedione or combinations thereof, to the individual.

13. The method of claim 1, wherein the individual has been tested for the presence of islet autoantibodies, wherein the presence of islet autoantibodies is indicative of the presence, or likely development of, T1D.

14. A method of selectively treating type 1 diabetes (T1D) in an individual comprising:

(a) selecting an individual for treatment with D-α-methyldopa on the basis of the individual with a DQ8 allele having islet autoantibodies that recognize an islet antigen selected from insulin, glutamic acid decarboxylase, insulinoma associated antigen 2, and zinc transporter 8, detectable in a blood sample from the individual and;

(b) administering a pharmaceutical composition comprising D-α-methyldopa to the individual.

15. The method of claim 3, wherein the pharmaceutical composition comprises less than 10%, by weight, of L-α-methyldopa.

16. The method of claim 3, wherein the pharmaceutical composition comprises less than 1%, by weight, of L-α-methyldopa.

* * * * *

UNITED STATES PATENT AND TRADEMARK OFFICE
CERTIFICATE OF CORRECTION

PATENT NO. : 9,820,957 B2
APPLICATION NO. : 15/466026
DATED : November 21, 2017
INVENTOR(S) : Steve Orndorff, Aaron Michels and Peter Gottlieb Page 1 of 1

It is certified that error appears in the above-identified patent and that said Letters Patent is hereby corrected as shown below:

In the Claims

In Column 14, Claim 1, Lines 45-51, please delete:
"A method of treating, ameliorating, or slowing the progression or development of an type 1 diabetes (T1D) selected from autoimmune diabetes or Celiac disease in an individual having a DQ8 allele by administering to an individual in need of such treatment, a therapeutically effective amount of D-α-methyldopa, or a pharmaceutically acceptable salt, solvate, or hydrate thereof."

And insert:
--A method of treating, ameliorating, or slowing the progression or development of an autoimmune disease selected from type 1 diabetes (T1D) or Celiac disease in an individual having a DQ8 allele by administering to an individual in need of such treatment, a therapeutically effective amount of D-α-methyldopa, or a pharmaceutically acceptable salt, solvate, or hydrate thereof.--

Signed and Sealed this
Twentieth Day of February, 2018

Andrei Iancu
*Director of the United States Patent and Trademark Office*